United States Patent
Bajaj et al.

[11] Patent Number: 6,056,765
[45] Date of Patent: May 2, 2000

[54] LANCET DEVICE

[76] Inventors: Ratan Bajaj, 3067 Mountain Dr., Fremont, Calif. 94536; Scott T. Kaminski, 121 Samoa Ct., San Ramon, Calif. 94583

[21] Appl. No.: 09/103,058

[22] Filed: Jun. 23, 1998

Related U.S. Application Data

[60] Provisional application No. 60/050,595, Jun. 24, 1997.

[51] Int. Cl.[7] ................................................. A61B 17/14
[52] U.S. Cl. ........................... 606/181; 606/182; 606/183
[58] Field of Search ................................. 606/181, 182, 606/183, 184, 185, 167

[56] References Cited

U.S. PATENT DOCUMENTS

| | | | |
|---|---|---|---|
| Re. 32,922 | 5/1989 | Levin et al. | 606/182 |
| 2,332,107 | 10/1943 | Neibergs | 128/327 |
| 2,387,428 | 11/1945 | Brothers | 128/327 |
| 3,507,270 | 4/1970 | Ferrier | 128/2.05 |
| 4,416,279 | 11/1983 | Lindner et al. | 606/182 |
| 4,653,513 | 3/1987 | Dombrowski | 128/765 |
| 5,366,470 | 11/1994 | Ramel | 606/183 |
| 5,540,709 | 7/1996 | Ramel | 606/183 |

FOREIGN PATENT DOCUMENTS

| | | |
|---|---|---|
| 118654 | 5/1877 | France . |
| 478849 | 1/1916 | France . |
| 0012486 | of 1909 | United Kingdom . |

Primary Examiner—Michael Buiz
Assistant Examiner—Lien Ngo
Attorney, Agent, or Firm—George W. Wasson

[57] ABSTRACT

A lancet device that includes an adjustable digit-constricting member movably and operatively coupled with an outer (first) barrel. An inner (second) barrel, rigidly mounted inside the outer barrel, houses a biasing element attached thereto as well as a lancet attached to the biasing element.

21 Claims, 4 Drawing Sheets

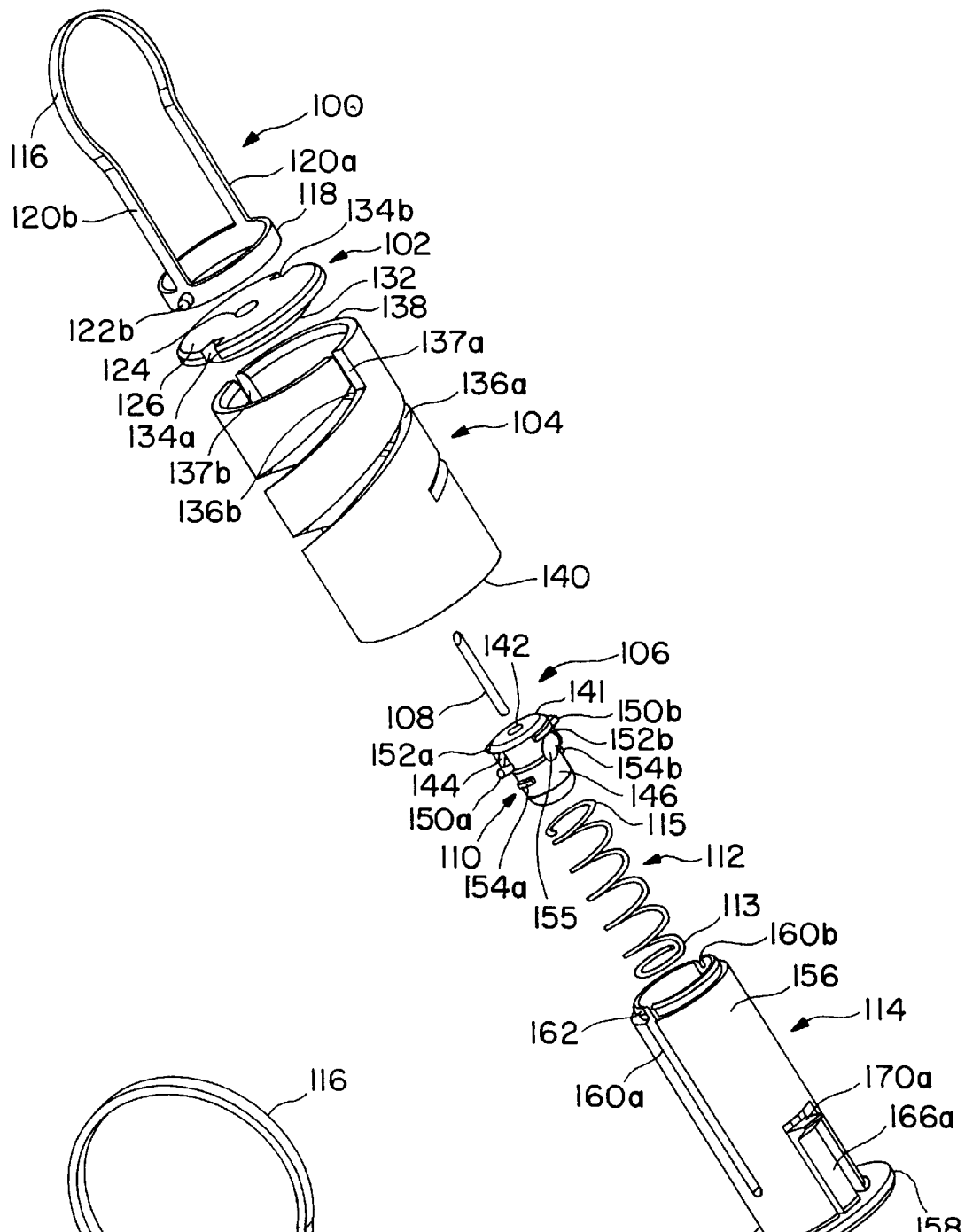
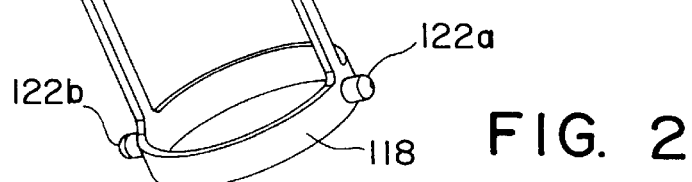

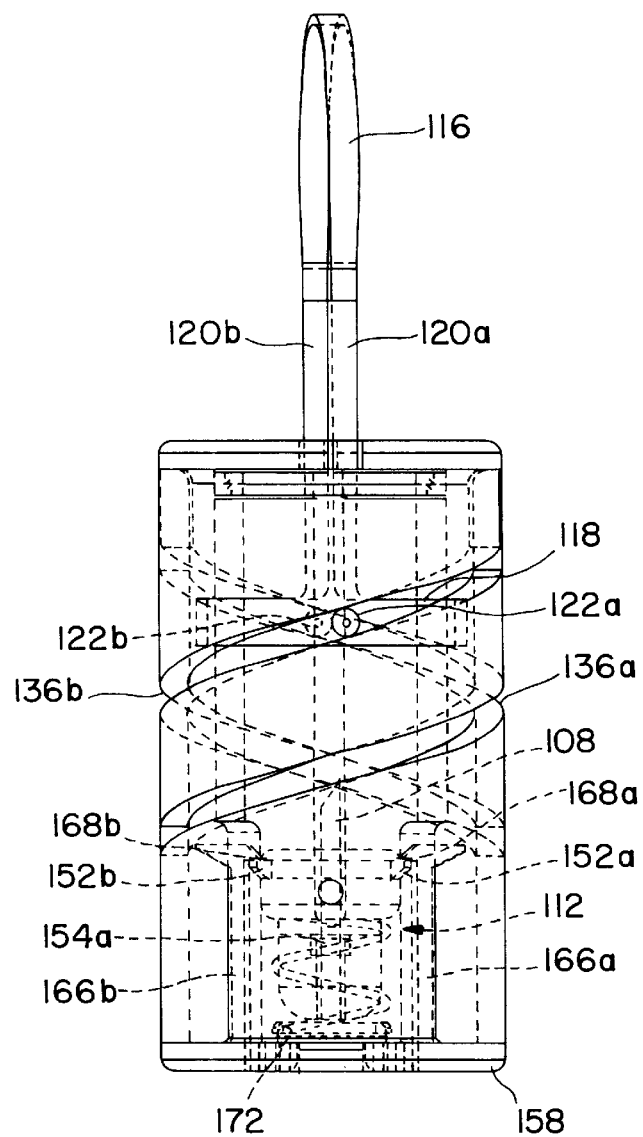
FIG. 6
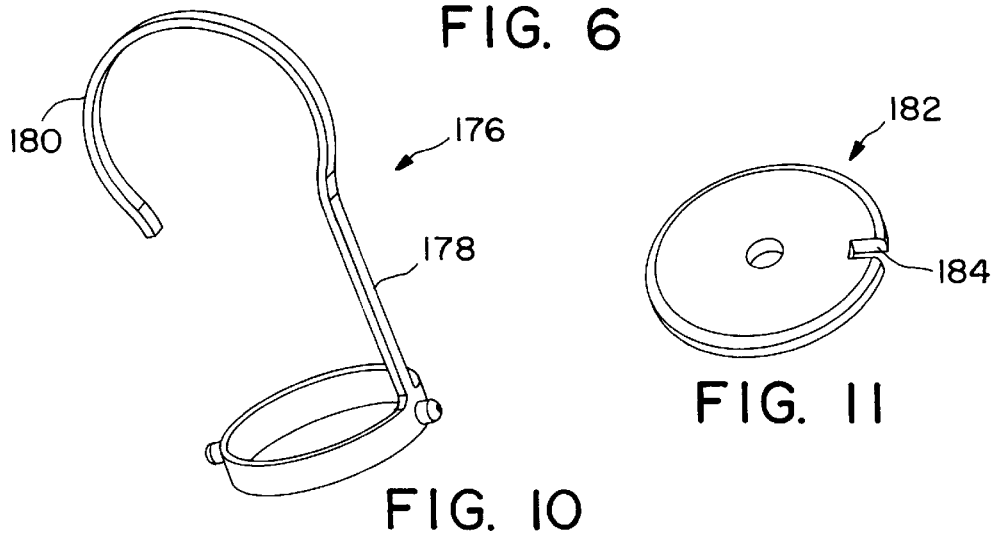
FIG. 10
FIG. 11

LANCET DEVICE

CROSS-REFERENCE TO RELATED APPLICATIONS

This application claims the benefit of U.S. Provisional Application Ser. No. 60/050,595 filed Jun. 24, 1997.

STATEMENT REGARDING FEDERALLY-SPONSORED RESEARCH OR DEVELOPMENT

Not Applicable

REFERENCE TO MICROFICHE APPENDIX

Not Applicable

BACKGROUND OF THE INVENTION

This invention relates to the field of blood-sampling devices, particularly to a disposable, pre-armed lancet device capable of constricting the finger from which the blood is to be drawn.

For purposes of medical diagnosis it is often necessary for patients to provide small specimens of blood to be analyzed. When it is required that such analyses be performed on a routine basis, as is often the case with patients suffering from diabetes or those diagnosed with the Human Immunodeficiency Virus, patients may have to obtain blood specimens without the help of a nurse or other assistant. Several disposable apparatus allowing patients to collect blood samples without the aid of others are available. Since all such devices obtain the blood by producing a small incision in the skin of the patient (most commonly the skin of one of the digits of the hand) with a sharp lancet, it is imperative that devices of this type be executed in a manner which allows them to be safely disposed after use without risking injury and possible infection to the persons who may come into contact with these devices after their disposal. Another desirable feature of instruments for collection of blood samples is the inability of the patient to anticipate the incision and to attempt to withdraw therefrom.

Even though the makers of known blood-sampling devices have attempted to address the above-mentioned concerns by providing safer and more convenient instruments, prior-art units continue to fall short in several areas. Significantly, prior-art devices require the patient (or the assistant) to either manually squeeze the blood from the incision or to employ a separate tourniquet for this purpose, thus complicating the procedure and making it more stressful for the patient. Additionally, if the act of squeezing the blood from the incision is manually performed by an assistant who massages the skin around the incision, the contact with the blood of the patient, even when made by the assistant's hands protected with surgical gloves, presents the assistant with a risk of infection. Furthermore, obtaining a blood sample from the patient's finger using a conventional lancet device often causes the patient to experience a painful sensation. This occurs when the incision in one of the digits of the patient's hand is made so that the lancet strikes too close to the bone (e.g., the distal phalanx) of the digit.

BRIEF SUMMARY OF THE INVENTION

It is accordingly desirable to provide a lancet device that allows to minimize the pain caused by the incision.

It is also desirable to provide a lancet device that increases the efficiency with which blood is collected from the incision without unnecessary discomfort to the patient or additional risk of infection to the assistant gathering the blood sample, if such an assistant is utilized.

Other advantages of the invention will become apparent after consideration of the ensuing description and the accompanying drawings.

In one embodiment of the invention, the lancet device comprises an adjustable digit-constricting member that is movably and operatively coupled to an outer (first) barrel. An inner (second) barrel, rigidly mounted inside the outer barrel, houses a biasing element attached thereto and a lancet attached to the biasing element.

BRIEF DESCRIPTION OF THE SEVERAL VIEWS OF THE DRAWING

The present invention is illustrated by way of example, and not by way of limitation, in the figures of the accompanying drawings, where:

FIG. 1 is an exploded perspective view of a lancet device in accordance with one embodiment of the present invention.

FIG. 2 is a perspective view of the digit-constricting member illustrated in FIG. 1.

FIG. 6 is a side elevational view of the lancet device of FIG. 1 in assembled state.

FIG. 10 is a perspective view of an alternative embodiment of the digit-constricting member of FIG. 2.

FIG. 11 is a perspective view of an alternative embodiment of the end-cap of FIG. 3.

For purposes of illustration, these figures are not necessarily drawn to scale. In all of the figures, same components are designated by the same reference numerals.

DETAILED DESCRIPTION OF THE INVENTION

Figure 3:
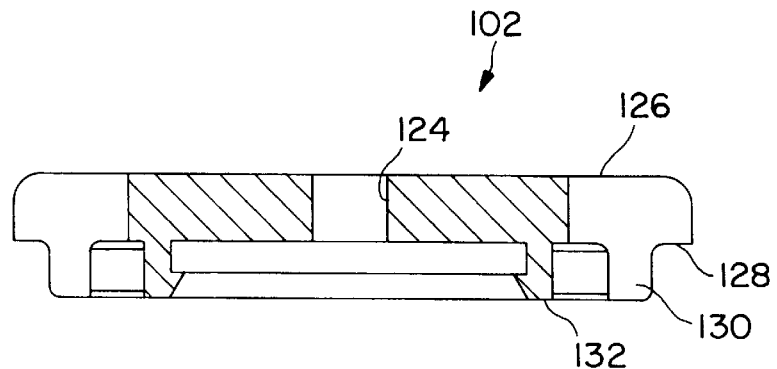
FIG. 3 is a cross-sectional view of the end-cap illustrated in FIG. 1.

Throughout the following description, specific details are set forth in order to provide a more thorough understanding of the invention. However, the invention may be practiced without these particulars. In other instances, well-known elements have not been shown or described to avoid unnecessarily obscuring the invention. Accordingly, the specification and drawings are to be regarded in an illustrative, rather than a restrictive, sense.

FIG. 1 illustrates the lancet device according to one embodiment of the present invention. The lancet device includes a digit-constricting member 100, an end-cap 102, and outer (first) barrel 104, a lancet 106 comprising a needle 108 and a needle holder 110, a biasing element or spring 112 having a proximal end 113 and a distal end 115, and an inner (second) barrel 114.

Digit-constricting member 100 is shown with greater detail in FIG. 2. Member 100 has a loop (tourniquet) portion 116 and a band (trigger) portion 118, interconnected by parallel arms 120a and 120b. Cylindrical protuberances 122a and 122b are formed on the exterior surface of band portion 118 and are diametrically opposed to each other.

As shown in FIG. 3, end-cap 102 has a centrally-located through aperture 124, a flat top surface 126, and a flat bottom surface 128. Surface 128 supports a continuous flange 130 and a continuous snap-fit element 132. Flange 130 and element 132 are concentric with aperture 124, the diameter of flange 130 being greater than that of element 132. As evident from FIG. 1, end-cap 102 also contains diametrically-opposed peripheral cut-outs 134a and 134b.

Outer barrel 104 (FIG. 1) contains a pair of helical slots or grooves 136a and 136b, extending from an open distal end 138 of the barrel toward its open proximal end 140. Slots 136a and 136b have corresponding longitudinal entrance portions 137a and 137b.

Figure 4:
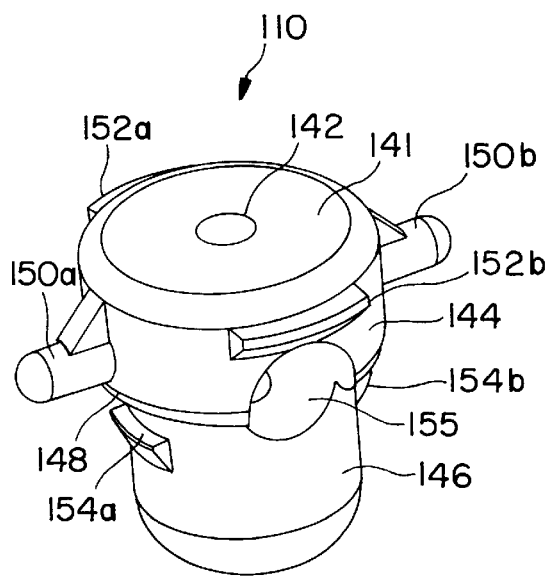
FIG. 4 is a perspective view of the needle holder illustrated in FIG. 1.

Needle holder 110, shown in FIG. 4, includes a flat upper surface 141 with a longitudinal, centrally-disposed through opening 142 formed therethrough, an upper cylindrical portion 144, and a lower cylindrical portion 146 having a smaller diameter than portion 144. A shoulder 148 forms the junction between portions 144 and 146. Upper cylindrical portion 144 bears diametrically-opposed cylindrical protuberances 150a and 150b as well as diametrically-opposed projections 152a and 152b, oriented at a right angle with respect to protuberances 150a and 150b. Diametrically-opposed projections 154a and 154b are formed on the cylindrical surface of portion 146. A transverse service opening 155, formed in the side of needle holder 110, ties into opening 142.

Figure 5:
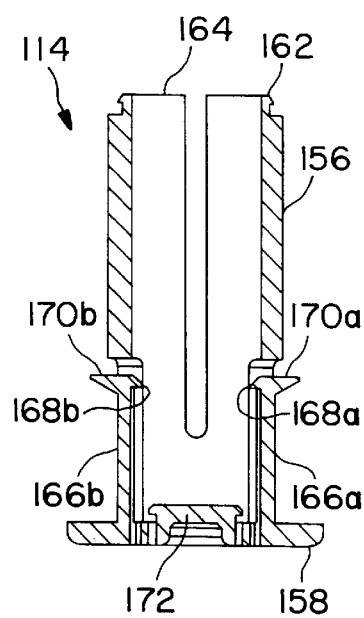
FIG. 5 is a cross-sectional view of the inner barrel illustrated in FIG. 1.

Inner barrel 114 (FIG. 5) has a hollow cylindrical body 156 and a base 158 located at the proximal end of the barrel. Cylindrical body 156 contains a pair of diametrically-opposed longitudinal slots 160a and 160b, illustrated in FIG. 1. Referring back to FIG. 5, a continuous snap-fit element 162 is formed along the distal end 164 of barrel 114. Cylindrical body 156 encorporates a retaining catch comprising bendable arms 166a and 166b with internally-facing detents 168a and 168b and axial-loading faces 170a and 170b. Base 158 includes an internally-facing, centrally-located tooth element 172.

In one embodiment of the invention, digit-constricting member 100, end-cap 102, outer barrel 104, needle holder 110, and inner barrel 114 are injection-molded plastic pieces. Needle 108 is made of stainless steel.

The assembly of the lancet device according to one embodiment of the invention may be illustrated by reference to FIGS. 1 through 6. Initially, outer barrel 104 is glued or ultrasonically welded to base 158 of inner barrel 114, thus forming a double-wall cylinder with a common base. Needle 108 is then inserted into central opening 142 of needle holder 110 and is glued in place with a drop of glue placed into service opening 155. It is notable that the depth of the incision provided by the lancet device according to the invention is determined by the difference between the distance from the tip of needle 108 to surface 141 of the needle holder and the thickness of end-cap 102. Depending on the requirements, the former dimension may be easily adjusted by varying the insertion depth of needle 108 into opening 142.

Following the assembly of lancet 106, lower cylindrical portion 146 of needle holder 110 is inserted into the coils comprising the distal end 115 of spring 112 until the coils of the spring are gripped by projections 154a and 154b, attaching the spring to needle holder 110. The subassembly comprising lancet 106 and spring 112 is then inserted into the subassembly comprising outer barrel 104 and inner barrel 114 by first aligning protuberances 150a and 150b of the needle holder with mating longitudinal slots 160a and 160b and then pressing lancet 106 into barrel 114 in the direction of base 158 until the coils of proximal end 113 of the spring become fixedly engaged by tooth element 172 and detents 168a and 168b of the inner barrel interlock with mating projections 152a and 152b of needle holder 110. Lancet 106 is thereby secured in the armed position, with the coils of distal end 115 of compressed spring 112 pressing against shoulder 148 of needle holder 110 and the coils of the proximal end 113 of the spring pressing against the interior surface of base 158.

After arming the lancet, digit-constricting member 100 is positioned between outer barrel 104 and inner barrel 114 by inserting protuberances 122a and 122b of band portion 118 into corresponding longitudinal entrance portions 137a and 137b of slots 136a and 136b. Finally, end-cap 102 is placed between arms 120a and 120b of digit-constricting member 100 such that corresponding cut-outs 134a and 134b of the end-cap accommodate the aforementioned arms. Pressure, directed toward base 158, is then exerted on the end-cap, allowing snap-fit element 132 of the end-cap to interlock with corresponding snap-fit element 162 of barrel 114, rotationally coupling end-cap 102 and inner barrel 114. Continuous flange 130 of end-cap 102 fits inside outer barrel 104 and the distal end 138 of the barrel abuts bottom surface 128 of the end-cap, thus preventing withdrawal of band portion 118 of digit-constricting member 100 from the assembly comprising outer barrel 104 and inner barrel 114. The assembled lancet device in the armed position is shown in FIG. 6.

Figure 7:
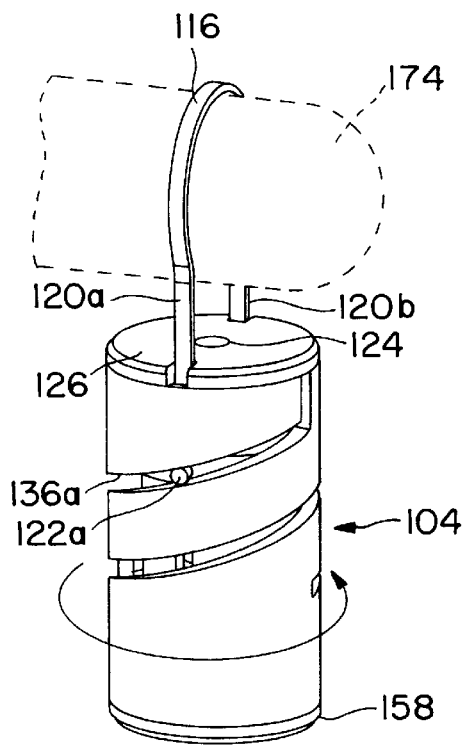
FIG. 7 is a perspective view showing the lancet device of FIG. 1 as a patient's finger is being positioned therein.
Figure 8:
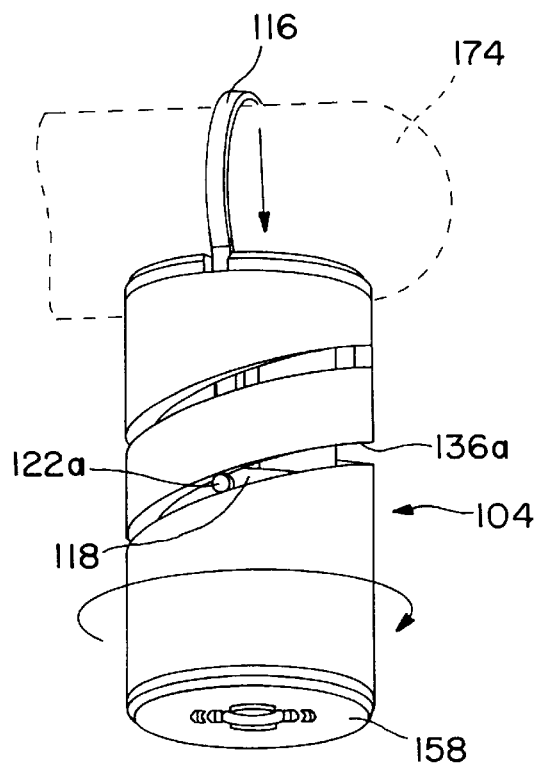
FIG. 8 is a perspective view showing the lancet device of FIG. 7 as it is being tightened around the patient's finger.
Figure 9:
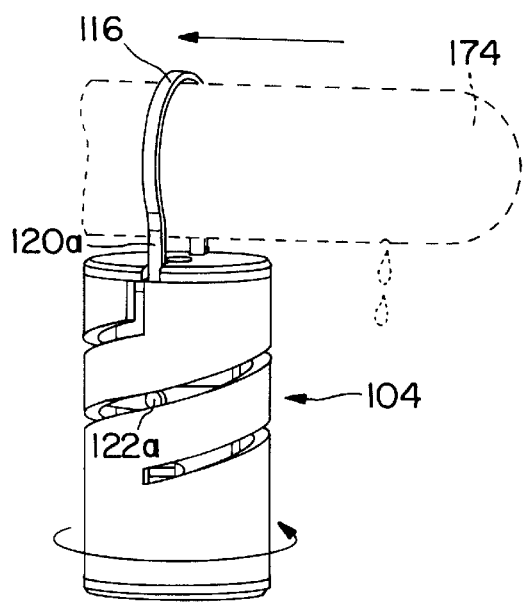
FIG. 9 is a perspective view illustrating the repositioning and re-tightening procedure of the lancet device of FIG. 7.

The operation of the lancet device is discussed with reference to FIGS. 1 and 7 through 9. To collect a blood sample, a finger or digit 174 is initially inserted into loop portion 116 of digit-constricting member 100. Outer barrel 104 is then rotated with respect to the finger as shown in FIG. 7, causing protuberances 122a and 122b to engage with and travel along corresponding helical slots 136a and 136b. This motion of digit-constricting member 100 with respect to outer barrel 104 causes loop portion 116 of member 100 to travel toward the upper surface of end-cap 102, tightening around finger 174 (FIG. 8). The tightening of loop portion 116 causes the skin to swell out at the desired location of the puncture.

Further rotation of outer barrel 104 presses band portion 118 of member 100 against axial loading faces 170a and 170b, causing arms 166a and 166b to deflect outwardly (laterally) until detents 168a and 168b release projections 152a and 152b of the needle holder, at which time lancet 106 fires (is discharged) towards finger 174. Thus, digit-constricting member 100 is a control member that serves not only as a means for constricting the patient's finger, but also as a means for discharging the lancet to make the incision in the abovementioned finger. As lancet 106 is propelled towards the finger by the extending spring, it is guided by protuberances 150a and 150b, slidingly engaging longitudinal slots 160a and 160b. As the extension of spring 112 reaches its maximum point, needle 108 momentarily protrudes through aperture 124 of the end-cap and pierces the skin of the finger, producing an incision of a desired size and shape in accordance with the size and shape of needle 108. As the incision is being made, the level of discomfort experienced by the patient is minimized since the swelling of the skin at the point of the incision, caused by the tightening of loop portion 116, prevents the needle from striking too close to the bone of the finger.

Upon making the incision, lancet 106 is forced to retract into the chamber, defined by inner barrel 114 and end-cap 102, by the spring seeking to return to its neutral position. Spring 112, opposite ends of which remain attached to needle holder 110 and base 158 of inner barrel 114, ensures that the tip of needle 108 remain below top surface 126 of the end-cap. Since the construction of the lancet device is such that the instrument cannot be disassembled and re-armed, the device may at this point be safely disposed without risking injury and infection to individuals who may come into contact with the lancet device.

Once the incision has been made, outer barrel 104 may be rotated in the opposite direction to that indicated in FIGS. 7 and 8, causing loop 116 to loosen around the finger. Loop 116 can then be moved farther back along the finger and re-tightened (FIG. 9) by rotating barrel 104 as shown. The re-tightening of the strap causes blood to be forced out of the puncture previously made, and allows multiple drops of blood to be collected for analysis. The patient can perform this procedure single-handedly, eliminating the need for his/her assistant to manually stroke the finger in order to obtain the desired amount of blood from the incision. Additionally, the risk of infection to the assistant is eliminated in the process. Furthermore, more blood can be drawn from the incision in a more expedient manner, thus minimizing discomfort of the patient.

Once the desired amount of blood has been collected, loop 116 is loosened and the lancet device is discarded.

The above configurations of the lancet device are given only as examples and other variations of the device are possible. For instance, FIG. 10 shows an alternative embodiment of the invention having a digit-constricting member 176 that includes a longitudinal arm 176 terminating in a hook member 178. Digit-constricting member 176 is designed to mate with an end-cap 182, illustrated in FIG. 11. End-cap 182 includes a single peripheral cutout 184 configured to accommodate arm 178. Therefore, the scope of the invention should be determined not by the specific examples given, but by the appended claims and their equivalents.

What is claimed is:

1. A lancet device comprising:
    a digit-constricting member;
    a first barrel movably and operatively coupled with said digit-constricting member;
    a second barrel attached to said first barrel;
    a biasing element attached to said second barrel; and
    a lancet attached to said biasing element.

2. The lancet device of claim 1 wherein:
    said first barrel has a proximal end and a distal end;
    said second barrel is rigidly attached to said first barrel, said second barrel having a proximal end and a distal end;
    said biasing element has a proximal end and a distal end, the proximal end of said biasing element coupled to said second barrel; and
    said lancet is coupled to the distal end of said biasing element.

3. The lancet device of claim 2 wherein said second barrel is concentrically and fixedly positioned within said first barrel.

4. The lancet device of claim 3 further including an end-cap rotationally attached to the proximal end of said second barrel, said end-cap having a centrally-located aperture.

5. The lancet device of claim 3 wherein said first barrel has a helical path defined therealong.

6. The lancet device of claim 5 wherein said digit-constricting member comprises a loop portion and a band portion, said band portion concentrically disposed between said first barrel and said second barrel, said band portion further including a protuberance disposed in said helical path and movably engaging therewith.

7. The lancet device of claim 2 wherein said lancet and said biasing element are disposed inside said second barrel, said second barrel further including a retaining catch, the lancet device assembled with said biasing element being compressed between said lancet, releasably captured by said retaining catch, and the proximal end of said second barrel.

8. The lancet device of claim 7 wherein said lancet is propelled toward the distal end of said first barrel by said biasing element when said digit-constricting member releases said retaining catch.

9. A disposable lancet device for drawing blood from a finger, said disposable lancet device comprising:
    an outer barrel having a proximal end and a distal end;
    an inner barrel having a proximal end and a closed distal end, said inner barrel concentrically disposed inside said outer barrel and rigidly interconnected therewith;
    a spring having a proximal end and a distal end, the proximal end of said spring attached at the closed distal end inside said inner barrel;
    a lancet attached to the distal end of said spring; and
    finger-and-lancet control means, movably and operatively coupled with said outer barrel, for constricting said finger and for discharging said lancet to make an incision in said finger.

10. The disposable lancet device of claim 9 further including an end-cap attached to the distal end of said inner barrel, said end-cap having at least one peripheral cut-out and a centrally-located aperture sized to allow said lancet to momentarily protrude therethrough immediately after said lancet has been discharged by said control means.

11. The disposable lancet device of claim 9 wherein said outer barrel has a pair of helical tracks formed therealong.

12. The disposable lancet device of claim 11 wherein said control means comprises a tourniquet member and a trigger member, said trigger member concentrically and movably disposed between said outer barrel and said inner barrel, said trigger member further including a pair of protuberances each disposed within one of said pair of helical tracks and movably engaging therewith.

13. The disposable lancet device of claim 12 wherein said tourniquet member gradually constricts said finger as said pair of protuberances of said trigger member is advanced along said pair of helical tracks from the distal end toward the proximal end of said outer barrel by rotating said outer barrel with respect to said control means.

14. The disposable lancet device of claim 13 wherein said inner barrel includes a retaining catch, the disposable lancet device assembled with said spring being compressed between said lancet, releasably captured by said retaining catch, and the closed proximal end of said inner barrel, said trigger member capable of exerting a specific force on said retaining catch as said pair of protuberances of said trigger member is advanced along said pair of helical tracks from the distal end toward the proximal end of said outer barrel by rotating said outer barrel with respect to said control means, said retaining catch being released when said trigger member exerts said specific force on said retaining catch, causing said lancet, biased by said spring, to discharge and make an incision in said finger.

15. The disposable lancet device of claim 14 wherein said spring possesses a specific tensile force, said lancet being instantly and completely retracted inside said inner barrel after making said incision by said specific tensile force of said spring to prevent any further accidental incisions from occurring.

16. The disposable lancet device of claim 12 wherein said tourniquet member comprises a continuous loop.

17. The disposable lancet device of claim 12 wherein said tourniquet member comprises a rigid arm having a curved end.

18. A disposable, single-use, pre-armed lancet device for drawing blood from a finger by making an incision therein, said incision having a controlled depth, said lancet device comprising:

an outer barrel having a pair of helical slots formed therealong, an open proximal end, and an open distal end;

a lancet comprising a needle mounted in a needle holder, said needle holder having at least one protuberance, said needle having a length;

an inner barrel having an open proximal end, a closed distal end, a retaining catch, and at least one longitudinal slot, said at least one protuberance movably disposed in said at least one longitudinal slot, said inner barrel concentrically disposed inside said outer barrel, the proximal ends of said inner and outer barrels being rigidly interconnected, the open distal end of said inner barrel having a first snap-fit element;

a spring having a proximal end and a distal end, said spring and said lancet located inside said inner barrel, the proximal end of said spring attached to the closed distal end of said inner barrel, the distal end of said spring attached to said needle holder;

a finger-and-lancet control means, movably and operatively coupled with said outer barrel, for constricting said finger and for discharging said lancet to make an incision in said finger, said control means including a tourniquet member and a trigger member, said trigger member concentrically and movably disposed between said outer barrel and said inner barrel, said trigger member having a pair of protuberances each disposed within one of said pair of helical slots and movably engaging therewith; and an end-cap having a thickness, a second snap-fit element, at least one peripheral cut-out to accommodate said trigger member, and a centrally-located aperture sized to allow said needle to momentarily protrude therethrough to make said incision, said controlled depth of said incision being determined by the length of said needle and by the thickness of said end-cap, said end-cap rotationally attached to the distal end of said inner barrel by interlocking of said first and second snap-fit elements, said pair of protuberances unable to disengage said pair of helical slots at the distal end of said outer barrel due to said end-cap being attached to said inner barrel.

19. The lancet device of claim 18 wherein said retaining catch comprises at least one bendable arm having an internally-facing detent and an axial-loading face; said needle holder having at least one projection formed thereon; the lancet device assembled with said spring being compressed between said needle holder, said at least one projection releasably captured by said at least one internally-facing detent, and the closed proximal end of said inner barrel; said trigger member capable of exerting a specific force on said at least one axial-loading face as said pair of protuberances is advanced along said pair of helical slots toward the proximal end of said outer barrel by rotating said outer barrel with respect to said control means; said internally-facing detent releasing the projection of said needle holder when said trigger member exerts said specific force on said at least one axial-loading face and deflects said bendable arm, thus causing said lancet, biased by said spring, to discharge and make an incision in said finger.

20. The lancet device of claim 18 wherein said tourniquet member comprises a continuous loop.

21. The lancet device of claim 18 wherein said tourniquet member comprises a rigid arm having an end curved to accommodate a human digit.

* * * * *